United States Patent [19]

Larock

[11] Patent Number: 4,535,179

[45] Date of Patent: Aug. 13, 1985

[54] SYNTHESIS OF BICYCLIC AND TRICYCLIC 7-OXA PROSTAGLANDIN ENDOPEROXIDE ANALOGS VIA OXYPALLADATION OF NORBORNADIENE

[75] Inventor: Richard C. Larock, Ames, Iowa

[73] Assignee: Iowa State University Research Foundation Inc., Ames, Iowa

[21] Appl. No.: 471,760

[22] Filed: Mar. 3, 1983

[51] Int. Cl.$^3$ .......................................... C07C 177/00
[52] U.S. Cl. ................................. 560/117; 560/120; 562/499; 562/502
[58] Field of Search ............... 560/117, 120; 562/499, 562/502

[56] References Cited

U.S. PATENT DOCUMENTS 4,113,755 9/1978 Larock ................................ 260/429
4,351,949 9/1982 Larock ................................ 548/359

OTHER PUBLICATIONS

Larock et al., Tet. Letters, 23, 1071, 715, (1982).
March, Advanced Organic Chemistry, 2nd ED., pp. 284–302, (1977).

Primary Examiner—Robert Gerstl
Attorney, Agent, or Firm—Zarley, McKee, Thomte, Voorhees & Sease

[57] ABSTRACT

Bicyclic oxa prostaglandin endoperoxide analogs, and tricyclic oxa prostaglandin analogs are prepared by reacting norbornadiene palladium dichloride with tertiary butyl-6-hydroxyhexanoate in an oxypalladation reaction to provide an oxypalladium intermediate which can subsequently be elaborated into bicyclic and/or tricyclic 7-oxa prostaglandin endoperoxides. If the intermediate is carbonylated in the presence of an organic amine, preferably diisopropylethylamine, the compound is bicyclic; if the amine is eliminated, the compound is tricyclic. The analogs are novel compounds.

7 Claims, No Drawings

SYNTHESIS OF BICYCLIC AND TRICYCLIC 7-OXA PROSTAGLANDIN ENDOPEROXIDE ANALOGS VIA OXYPALLADATION OF NORBORNADIENE

This invention was conceived under National Institutes of Health Grant AM 21795, as administered by the Department of Health and Human Services.

BACKGROUND OF THE INVENTION

Prostaglandins in which a methylene unit has been replaced by an oxygen have received considerable attention in the past. A number of 7-oxa analogs of the primary prostaglandins have been synthesized and generally they are known to exhibit substantial biological activity. See, e.g., R. G. McDonald-Gibson, J. D. Flack and P. W. Ramwell, *Biochem. J.*, 132,117 (1973). Typical examples of the biological activities shown include inhibition of $PGE_1$ induced smooth muscle contractions at various concentrations, inhibition of $PGE_2$ biosynthesis, inhibition of arachidonic acid induced platelet aggregation, and the like. In earlier literature, Fried, et al. have synthesized a wide variety of monocyclic prostaglandin analogs in which the C-7 methylene has been replaced by oxygen. See Fried, J.; Santhankrishnan, T.; Himizu, J.; Lin, C.-H.; Ford, S. *Nature* 1969, 223, 208; Fried, J.; Mehra, M.; Kao, W.; Lin, C.-H, *Tetrahedron Lett.* 1970, 2695; Fried, J.; Mehra, M.; Kao, W. *J. Am. Chem. Soc.* 1971, 93, 5544; Fried, J.; Lin, C.; Mehra, M.; Kao, W.; Delven, P. *Ann. N.Y. Acad. Sci.* 1971, 180, 38; McDonald-Gibson, R. G.; Flack, J. D.; Ramwell, P. W. *Biochem. J.* 1973, 132, 117.

In view of the variety of activities of the compounds reported by Fried, the applicant has as a primary objective of the present invention, developed a new synthesis for bicyclic and tricyclic analogs of 7-oxa $PGH_2$.

In addition, the applicant has not only discovered a new high yield and direct synthesis technique for 7-oxa prostaglandin endoperoxide analogs, but has also discovered that one can selectively make either a bicyclic analog or a tricyclic analog, simply by the presence or absence of diisopropylethylamine in one of the reaction steps. This surprising discovery has not heretofore been known.

Accordingly, it is a primary objective of the present invention to prepare bicyclic and tricyclic 7-oxa prostaglandin endoperoxide analogs, which have a wide variety of biological activities.

A yet further objective of the present invention is to provide a synthesis technique for the preparation, selectively, of either bicyclic or tricyclic endoperoxide analogs, with the control of the synthesis of either a bicyclic or tricyclic being determined by, simply, the presence or absence of an organic amine, preferably diisopropylethylamine in one key reaction step.

A further objective is to provide a selective synthesis for bicyclic and/or tricyclic 7-oxa prostaglandin endoperoxide analogs which will progress in a high yield fashion to the desired synthesis products.

A further objective is to prepare a series of novel bicyclic and tricyclic 7-oxa prostaglandin endoperoxide analogs which exhibit a variety of biological activities, evidencing usefulness as pharmacological and potentially therapeutically active compounds.

SUMMARY OF THE INVENTION

A synthesis technique has been developed for 7-oxa bicyclic and/or tricyclic prostaglandin analogs. Preferably silver acetate assisted alkoxypalladation of norbornadiene palladium dichloride is conducted with tertiary butyl 6-hydroxyhexanoate to afford an alkoxy palladium complex. This complex, which cannot be isolated, can be carbonylated in methanol to afford an ester compound which is a useful intermediate in the synthesis of 7-oxa bicyclic and tricyclic prostaglandin analogs. Depending upon whether the carbonylation is conducted in the presence of an organic amine, preferably diisopropylethylamine or in the absence of such an amine, one can selectively prepare either the bicyclic or the tricyclic prostaglandin analog, respectively. The synthesis is thereafter completed via a sequence which involves selective ester hydrolysis, carboxylic acid reduction to an aldehyde, Wittig olefination, and if desired, an enone reduction.

The invention also relates to novel bicyclic and tricyclic oxa prostaglandin endoperoxide analogs of the formulas:

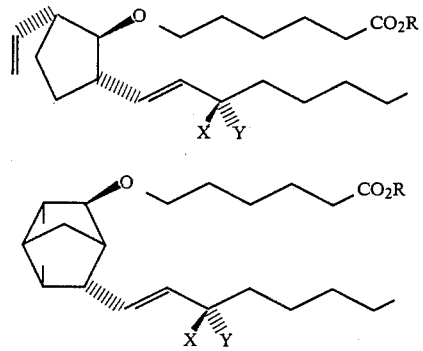

wherein R is selected from the group consisting of hydrogen, and lower $C_1$ to $C_8$ alkyl and "X" and "Y" are selected from the group of hydrogen and hydroxy and if either "X" or "Y" is hydrogen, the other is hydroxy, and the case of "X" and "Y" collectively, being a simple keto group.

Where X and Y are collectively a simple keto group, the enone reduction step is eliminated. Where one of X and Y is hydrogen and the other hydroxy, the synthesis includes a final enone reduction step.

DETAILED DESCRIPTION OF THE INVENTION

Bicyclic 7-oxa prostaglandin endoperoxide analogs of the present invention have the following general formula:

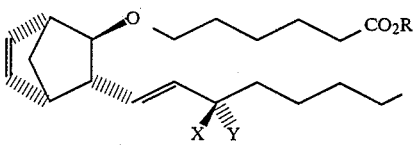

The tricyclic endoperoxide analogs of the present invention have the following formula:

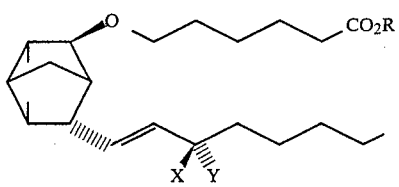

The definitions of "R" and "X" and "Y" for both the bicyclic and the tricyclic analogs are identical.

Preferably "R" is selected from the group of hydrogen, methyl and tertiary butyl. Tertiary butyl is a preferred group for the synthesis simply because it is a protecting group which will allow selective reaction at other sites on the molecule during the synthesis. One can prepare either hydroxy derivatives, i.e., one of X or Y is hydrogen and the other hydroxy, or simple keto derivatives where "X" and "Y" are collectively a keto group. Both are known to exhibit the desired biological activities. As will be apparent from the discussion of the synthesis technique below, if one desires to have X and Y equal H and OH, one must undergo a last enone reduction step wherein the keto group is reduced to a hydroxy group.

It has been surprisingly found that one can selectively control production of either bicyclic analogs or tricyclic analogs by the presence or absence of an organic amine, preferably diisopropylethylamine in one key reaction. If in the reaction synthesis, which is hereinafter described, there is diisopropylethylamine present in the carbonylation reaction step, one will prepare 7-oxa bicyclic prostaglandin analogs; on the other hand, if the diisopropylethylamine is eliminated, one will prepare 7-oxa tricyclic prostaglandin endoperoxide analogs. It is not presently known why the presence or absence of diisopropylethylamine controls the selective synthesis of either bicyclics or tricyclics; and indeed, this is one of the surprising aspects of the present invention.

The reaction scheme for the synthesis of the present invention is probably best illustrated by equations. Thus, the synthesis has somewhat artificially been broken into a series of numbered steps. Each of the steps will be described in conjunction with a reaction equation showing graphically the reaction which is occurring.

In the first step reaction, norbornadiene palladium dichloride is reacted with tertiary butyl 6-hydroxyhexanoate, preferably in a silver acetate assisted oxypalladation reaction to provide an oxy palladium intermediate compound. This step 1 reaction may be illustrated by the following equation:

Step 1: Reacting norbornadiene palladium dichloride with t-butyl 6-hydroxyhexanoate in an oxypalladation reaction.

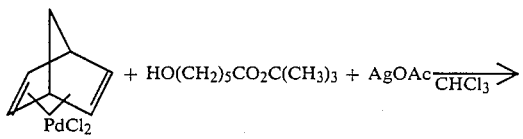

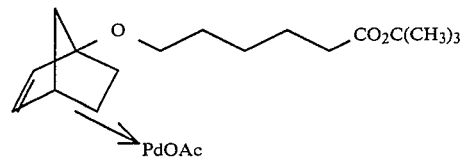

In this first step reaction, which is the same whether one is making either the bicyclic or the tricyclic compounds, the reaction can be described as an oxy-palladation reaction. It is illustrated in the equation as being conducted in the presence of chloroform, but methylene chloride solvent, or any other solvent for the individual reactants which is inert to the reactants, would be substantially suitable, such as ether or tetrahydrofuran. Temperature and pressure are not critical in this reaction.

Oxypalladation, although not the particular one shown in reaction step 1, has been heretofore known, see Stille, J. K.; Morgan, R. A. *J. Am. Chem. Soc.* 1966, 88, 5135. The referenced article, however, describes a methanol reaction as opposed to the reaction of the present invention, tertiary butyl-6-hydroxyhexanoate and it does not teach us that silver acetate should be added to the reaction.

The bicyclic oxypalladium intermediate formed in the reaction step 1 is not isolated, instead the second reaction step is simply conducted in the same reaction vessel. In the second reaction step, the intermediate is carbonylated to provide an ester intermediate which in part has the prostaglandin analog carbon skeletal structure. It is in this second carbonylating step which one selectively controls the preparation of either bicyclic analogs or tricyclic analogs. Surprisingly, and for reasons not fully understood by the applicant, if the carbonylation reaction is conducted in the presence of diisopropylethylamine, the reaction product will be a 7-oxa bicyclic prostaglandin analog. However, if the diisopropylethylamine is omitted from the carbonylation step, then the reaction product is a tricyclic 7-oxa prostaglandin analog. In practice, after the first step reaction has continued for a few minutes, carbon monoxide, preferably at one atmosphere pressure in the presence of methanol is added to the reaction vessel, preferably at low temperatures and allowed to warm. Again, temperature and pressure do not appear critical. However, it has been found convenient to cool the reaction vessel to $-78°$ C. and then gradually allow it to warm to room temperature during the carbonylation step. The carbonylation step, step 2, for purposes of the description herein, may be represented by the following equation:

Step 2: Carbonylating

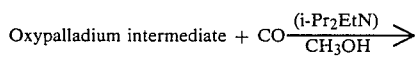

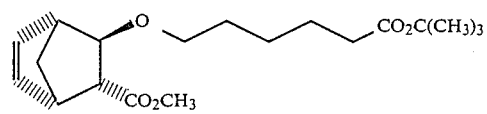

It is, as heretofore mentioned, surprising that in this carbonylation reaction, the presence or absence of the diisopropylethylamine, indicated as optional by the parentheses in the step 2 reaction equation, controls whether one forms a bicyclic compound or a tricyclic compound. In the reaction as illustrated in step 2, the diisopropylethylamine is indicated as present, and thus the reaction product formed is a bicyclic ester intermediate which in part has the basic prostaglandin analog carbon skeletal structure. The only difference in the synthesis of the two groups of compounds, that is, the bicyclics and the tricyclics, is the presence or absence of diisopropylethylamine in this second reaction step. All subsequent reaction steps for both, regardless of the ring structure, are identical. Thus, for convenience of description with regard to the reactions as set forth hereinafter, they will be presented only for the bicyclic, with the understanding that each step is identical and the reagents employed identical for preparation of the tricyclic compounds.

A carbonylation of an oxypalladium intermediate, without the presence of an amine, has been accomplished before, but not in the context of the present reaction. See, Hines, L. F.; Stille, J. K. J. Am. Chem. Soc. 1972, 94, 485. It is not believed that such a reaction has ever been conducted in the presence of diisopropylethylamine to provide bicyclic compounds as illustrated in the step 2 equation above.

The amount of diisopropylethylamine employed, where it is employed, is not critical, but generally excesses of the stoichiometric amount may be employed, even up to as much as five times the stoichiometric amount. One can also use organic amines other than the preferred diisopropylethylamine, such as triethylamine, with similar results. Likewise, it is preferred that an excess of carbon monoxide be bubbled through the reaction to allow completion of the carbonylation.

In the next and third step of the reaction, the ester intermediate, which in part has the basic prostaglandin analog carbon skeletal structure, is then selectively hydrolyzed to form an acid by saponification techniques. It can be illustrated by the following step 3 equation:

Step 3: Selective ester saponification

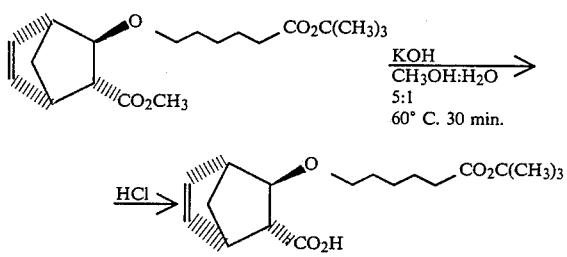

In the equation it can be seen that the methyl group of the ester intermediate, on the carbon atom adjacent the 7-oxa position, is removed, leaving a carboxylic acid group. Ester hydrolysis by saponification is, of course, a known and commonly employed organic synthesis reaction.

As illustrated, it is conducted in the presence of potassium hydroxide in a methyl alcohol-water solvent, preferably at a 5:1 ratio at a temperature of 60° C. for about 30 minutes. The reaction conditions may vary and do not appear critical in this saponification or ester hydrolysis step. The amount of potassium hydroxide employed is at least a stoichiometric amount, but preferably an excess of a stoichiometric amount.

After completing the acid hydrolysis as indicated in step 3, the just formed acid group, previously discussed, is next reduced to an aldehyde. This step in fact involves three distinct subparts, generally, anhydride formation, reduction to an alcohol, and then oxidation of the alcohol to an aldehyde, as illustrated in the equation below by the parentheses 1, 2 and 3, respectively, written above the equation. PCC stands for pyridinium chlorochromate. Again, reduction of an acid to an aldehyde is a technique, which has generally been known, although not in conjunction with the reaction of this invention. However, for general information concerning such reductions, see Corey, E. J.; Narasaka, K.; Shibasaki, M. J. Am. Chem. Soc. 1976, 98, 6417, which is incorporated herein by reference. Again, the reaction conditions do not appear critical, and temperature and pressure are not important, except to say that they can be used in a wide variety of conditions ranging from low temperatures up to room temperature.

Step 4: Acid to aldehyde reduction

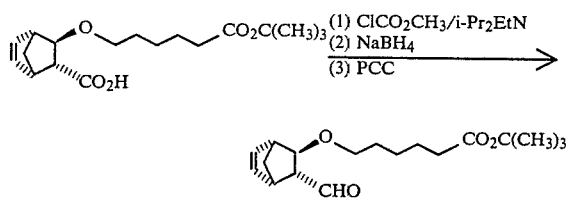

In the next step, after the aldehyde formation as indicated in the step 4 reaction, a Wittig olefination reaction is conducted at the reactive aldehyde site with 2-oxoheptyl phosphonate as illustrated by the following equation, showing the reaction to form an alpha, beta unsaturated ketone, which now has the complete carbon skeletal structure of the desired 7-oxa prostaglandin analog.

This Wittig olefination reaction is preferably conducted in the presence of an excess of the stoichiometric amount of the 2-oxoheptyl phosphonate, and in particular, it is desired if the amount be at least 1.5 equivalents. The reaction is preferably conducted in the presence of a solvent such as dimethoxyethane (DME).

As illustrated in the step 5 reaction equation, the resulting product is an enone which has the complete carbon skeletal structure of the desired prostaglandin analog. The ring structure on the left side of the enone product is shown as bicyclic, since diisopropylethylamine was utilized; however, if as previously explained, the diisopropylethylamine was omitted, the reaction sequence would be the same except a tricyclic structure would be present.

Step 5: Wittig olefination

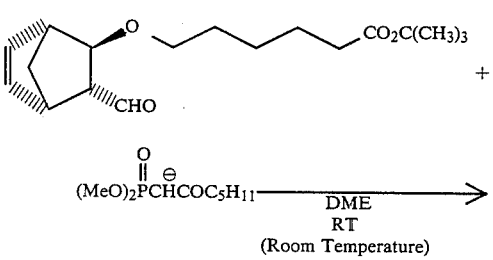

-continued

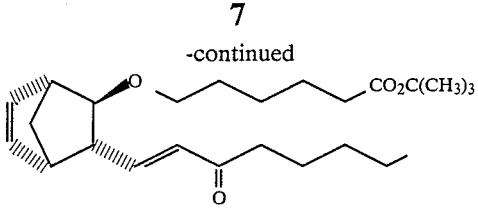

At this point, the reaction process of the invention can be thought of as complete. If desired, and if one wishes, one may conduct two additional steps. The first, referred to as step 6 herein, is an enone reduction to an allylic alcohol. That is to say, the keto group may be reduced to a hydroxy group if desired. This is similar to the reductions which have previously occurred, and can be illustrated by the following equation.

Step 6: Enone reduction to alcohol

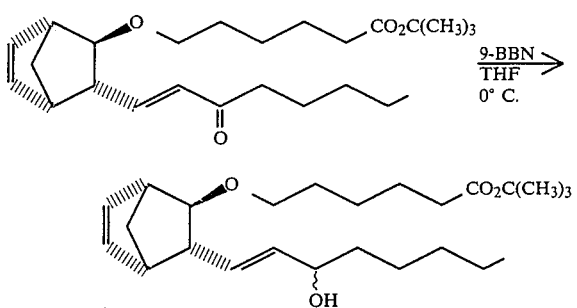

"BBN" refers to 9-borabicyclo[2.2.1]nonane. The conditions shown in the equation provide satisfactory results, but are not critical and a number of other reagents can be used.

Finally, if one desires to remove the tertiary butyl group which has protected the carboxyl moiety through the various steps heretofore described, one may do so by an ester hydrolysis similar to that previously described. Namely, hydrolysis of the tertiary alkyl ester can be accomplished by refluxing with potassium hydroxide in aqueous methanol for several hours, ideally within the range of two to four hours, and preferably 3.5 hours, followed by subsequent acidifidation as illustrated by the following step 7 equation.

Step 7: Ester hydrolysis to remove t-butyl group.

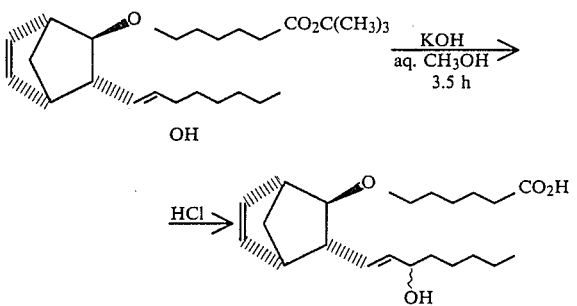

As heretofore stated, steps 6 and 7, that is, the enone reduction to the alcohol followed by the ester hydrolysis to remove the tertiary butyl group are entirely optional, those steps being run or not depending upon the desired functional groups on the 7-oxa prostaglandin endoperoxide analog.

As illustrated in the examples below, the process conditions for these reactions are simple, straightforward, non-complex and importantly produce the desired products in high yield. The result is an overall synthesis of 7-oxa prostaglandin endoperoxide analogs which have heretofore not existed.

The following examples are offered to further illustrate but not limit the invention. It should be understood that reasonable modifications both in the synthesis steps and techniques as well as the structures of the compounds, may be accomplished and the result would still come within the structure, function and operational results of the present invention.

EXAMPLES

For the following examples, reference will be made to the step numbers previously described in order to have a clear and graphic illustration of the reactions that are occurring.

Step 1: Norbornadienepalladium dichloride (270 mg, 1.00 mmol), 207 mg (1.10 mmol) of t-butyl 6-hydroxyhexanoate, and 183 mg (1.10 mmol) of silver acetate were stirred for one hour in 10 mL of methylene chloride and then filtered through Celite. After removal of the methylene chloride, 0.64 g (5.0 mmol) of di-iso-propylethylamine was added and the mixture was dissolved in 10 mL of methanol under nitrogen.

Step 2: After stirring for 10 minutes the mixture was cooled to $-78°$ C., flushed with carbon monoxide, and allowed to warm to room temperature overnight. The mixture was then diluted with ether, washed with water and saturated ammonium chloride, and dried over magnesium sulfate. Purification by flash chromatography provided 230 mg (68%) of the bicyclic carbonylated intermediate ester having in part the prostaglandin analogue carbon skeletal structure. Rf 0.30, hexanes:ethyl acetate (6:1); $^1$H NMR(CDCl$_3$) 1.4 [9H, s, C(CH$_3$)$_3$], 1.4–1.9 (8H, m), 2.18 (2H, t, J=6 Hz, CH$_2$CO), 2.6 (1H, t, J=3 Hz), 2.9 (1H, br), 3.1 (1H, br), 3.47 (2H, t, J=6 Hz, —CH$_2$O—), 3.63 (4H, s overlapping peaks, OCH$_3$, —CHO—), 6.05 (2H, m, vinyl); IR(neat) 1735 (C=O), 1635 (C=C), 730 (C=C)cm$^1$; m/z (real intensity) 282 (1), 217 (31), 185 (22), 151 (42), 115 (65), 66 (100).

A corresponding tricyclic compound was prepared similarly in 52% yield except that di-iso-propylethylamine was excluded. Rf 0.28, hexanes:ethyl acetate (5:1); $^1$H NMR(CDCl$_3$) δ 1.1–1.9 (11H, m), 1.4 [9H, s, (C(CH$_3$)$_3$], 1.9–2.3 (3H, m), 2.4 (1H, t, J=1 Hz), 3.3 (2H, t, J=6 Hz, —OCH$_2$—), 3.63 (3H, s, OCH$_3$), 3.7 (1H, s, —CHO). IR(neat) 1730 (C=O)cm$^{-1}$.

Step 3: The ester was next hydrolyzed. In particular, the ester product of step 2 (1.04 g, 3.07 mmol) and 0.54 g (9.6 mmol) of KOH were heated for 30 minutes at 60° C. in 30 mL of a 5:1 mixture of methanol and water. After diluting with ether, the reaction mixture was acidified with dilute HCl, washed with water and brine, and dried over magnesium sulfate. Purification by chromatography afforded 170 mg (16%) of the recovered ester, and 0.60 g (71%) of the acid (step 3 reaction product). Rf 0.35, hexanes:ethyl acetate:acetic acid (160:80:1); $^1$H NMR(CDCl$_3$) δ1.3–1.9 (8H, m), 1.4 [9H, s, —C(CH$_3$)$_3$], 2.2 (2H, t, J=6 Hz, —CH$_2$CO), 2.7 (1H, t, J=3 Hz), 2.8 (1H, br), 3.0 (1H, br), 3.45 (2H, —CH$_2$O), 3.6 (1H, br, —CHO—), 5.9–6.2 (2H, m, vinyl), 10.7 (1H, s, CO$_2$H); IR(neat) 1740 (ester C=O), 1715 (acid C=O), 1635 (C=C)cm$^{-1}$.

Step 4: The acid product of step 3 (0.36 g, 1.11 mmol), 0.42 g (4.4 mmol) of methyl chloroformate, and 0.65 g (5.0 mmol) of di-iso-propylethylamine were stirred in 18 mL of THF for one hour at 0° C. After removal of the THF, the crude product was dissolved in 32 mL of 6:1 THF-H$_2$O at 0° C., after which 0.25 g (6.6 mmol) of sodium borohydride was added. This was stirred for an additional hour. The reaction mixture was then diluted with ether, acidified with dilute HCl, washed with brine and dried over magnesium sulfate. Oxidation of the crude alcohol (0.42 g, 1.36 mmol) with 0.44 g (2.04 mmol) of pyridinium chlorochromate (PCC) using the procedure described by Corey (Corey, E. J.; Suggs, J. W. *Tetrahedron Lett.* 1975, 2647) which is incorporated herein by reference, was accomplished by stirring in 5 mL of methylene chloride for two hours. The mixture was then diluted with 25 mL of ether and decanted into a short Florisil column. The black residue from the flask was washed twice with 10 mL of ether and this was added to the column. Elution of the column with 500 mL of ether afforded 318 mg (76%) of the step 4 equation product: $^1$H NMR(CDCl$_3$) δ1.0-1.8 (8H, m), 1.43 [9H, s, —C(CH$_3$)$_3$], 2.17 (2H, t, J=6 Hz, —CH$_2$CO), 2.6 (1H, m), 2.9 (1H, br), 3.0 (1H, br), 3.3-3.5 (2H, m, —CH$_2$O—), 3.57 (1H, br s, —CHO—), 5.8-6.2 (2H, m, vinyl), 9.39 (1H, d, J=2 Hz, CHO); IR(neat) 2710 (CHO), 1740 (ester C=O), 1715 (aldehyde C=O)cm$^{-1}$.

Step 5: The synthesis of the reaction product of step 5 is representative of the Wittig olefination for the bicyclic analogue. Sodium hydride (67%) (51.4 mg., 1.43 mmol) was washed several times with hexanes under nitrogen. After drying for approximately five minutes under a gentle stream of nitrogen, this was suspended in 15 mL of DME. Dimethyl (2-oxoheptyl)phosphonate (0.370 g, 1.67 mmol) in 3 mL of DME was added, and the reaction was stirred for one hour. The reaction product of step 4 (275 mg, 0.892 mmol) in 3 mL of DME was then added via syringe. After stirring for three hours, 0.5 mL of acetic acid was added after which the solvent was removed with a rotary evaporator. The product was then extracted with 40 mL of hexanes and filtered through Celite. After concentration, chromatography of the residue afforded 265 mg (76%) of the enone olefination product containing the complete carbon skeleton of a 7-oxa prostaglandin endoperoxide analogue; Rf 0.33, hexanes:ethyl acetate (7:1); $^1$H NMR(CDCl$_3$) δ0.86 (3H, t, J=5 Hz, CH$_3$), 1.1-1.9 (13H, m), 2.0-3.0 (8H, m), 3.13 (1H, br s), 3.33 (2H, t, J=5 Hz, CH$_2$O), 6.00 (1H, d, J=15.5 Hz, =CHCO), 6.03 (2H, m, vinyl), 6.46 (1H, dd, J=8, 15.5 Hz, CH=CCO).

Step 6: The synthesis of the alcohols shown in the step 6 equation is representative of this reduction. The compound of step 5 (190 mg, 0.469 mmol) was dissolved in 6 mL of THF (tetrahydrofuran) and cooled to 0° C. A solution of 0.10 g (0.82 mmol) of 9-BBN in 2 mL of THF was added via syringe. After stirring for two hours at 0° C., 0.5 mL of methanol was added to destroy excess hydride. The boronic acid derivative was oxidized by addition of 0.27 mL of 3N aqueous sodium hydroxide followed by addition of 0.22 mL of 30% hydrogen peroxide. This mixture was then stirred for one hour after which it was diluted with ether, washed twice with brine and five times with water to remove 1,5-cyclooctanediol, and dried over magnesium sulfate. Purification by chromatography afforded 193 mg (100%) of the alcohol product: Rf 0.38, hexanes:ethyl acetate (3:1); $^1$H NMR(CDCl$_3$) δ0.9 (3H, t, J=6 Hz, CH$_3$), 1.1-2.5 (29H, m), 2.6-2.9 (2H, m), 3.1 (1H, br s), 3.38 (2H, t, J=6 Hz, CH$_2$O), 4.0 [1H, br, CH(OH)], 5.3-5.6 [2H, m, trans-CH=CHC(OH)], 5.9-6.2 (2H, m, cis-CH=CH); IR(neat) 3410 (OH), 1730 (C=O), 1140 (C—O)cm$^{-1}$.

Step 7: The final step, ester hydrolysis was conducted in the manner previously described with reference to the step 7 equation to remove the tertiary butyl group with the following results: 82% yield; Rf 0.29, hexanes:ethyl acetate:acetic acid (30:15:1); $^1$H NMR(CDCl$_3$) δ0.85 (3H, t, J=5 Hz, —CH$_3$), 1.0-2.0 (15H, m), 2.1-2.4 (4H, m), 2.5-2.9 (2H, m), 3.0 (1H, br s, —CHO—), 3.38 (2H, t, J=6 Hz, —CH$_2$O—), 3.8-4.1 [1H, br, CH(OH)], 5.2-5.5 (2H, m, trans-CH=CH—), 5.9-6.2 (2H, m, cis-CH=CH—); IR(neat) 3420 br(OH), 1715 (C=O), 1090 (C—O) cm$^{-1}$; $^{13}$C NMR(CDCl$_3$) 178.96, 137.86, 134,94, 134.03, 132.86, 86.23, 73.09, 69.00, 50.59, 47.67, 47.47, 46.95, 46.43, 46.24, 37.07, 33.95, 31.60, 29.46, 25.69, 25.04, 24.45, 22.57, 13.98; m/z 332.23574 (calcd for C$_{21}$H$_{32}$O$_3$, (M.$^+$ —H$_2$O), 332.23515).

With regard to the tricyclic products prepared in the absence of the diisopropylethylamine, similar and corresponding reactions were conducted to prepare corresponding tricyclic compounds with the following results. With regard to step 5, the compound was prepared wherein R=tertiary butyl and X and Y collectively equal a keto group with the following results: 99% yield; Rf 0.29, hexanes:ethyl acetate (7:1); δ0.87 (3H, t, J=5 Hz, CH$_3$), 1.0-2.6 (17H, m), 1.4 [9H, s, C(CH$_3$)$_3$], 3.3 (2H, t, J=6 Hz, CH$_2$O), 3.6 (1H, br s, CHO), 6.08 (1H, d, J=16 Hz, =CHCO), 6.78 (1H, dd, J=6, 16 Hz, CH=CCO).

The tricyclic compound wherein R is tertiary butyl and X is hydrogen and Y hydroxy, was prepared in accordance with the step 6 reaction to provide the following results: 100% yield; Rf 0.31, hexanes:ethyl acetate (3:1); $^1$H NMR(CDCl$_3$) δ0.87 (3H, t, J=5 Hz, CH$_3$), 1.0-2.4 (32H, m), 3.32 (2H, t, J=6 Hz, —CH$_2$O—), 3.67 (1H, br s, —CHO—), 4.0 (1H, br, —CHO—), 6.4-6.6 (2H, m, trans-CH=CH); IR(neat) 3410 (OH), 1730 (C=O)Cm$^{-1}$.

The compound of the immediately preceding paragraph was further modified by replacing the tertiary butyl group with a hydrogen, i.e., R=hydrogen and X=hydrogen with Y=hydroxy in the following manner: The compound just previously described (158 mg, 0.3886 mmol) and 0.22 g (3.9 mmol) of KOH were refluxed for 2.5 hours in 10 mL of 4:1 methanol —H$_2$O. After cooling, the reaction mixture was diluted with ether, acidified with dilute HCl, washed with brine, and dried over magnesium sulfate. Flash chromatography afforded 105 mg (77%) of the desired acid. Rf 0.26, hexanes:ethyl acetate:acetic acid (30:15:1); $^1$H NMR(CDCl$_3$) δ0.87 (3H, t, J=5 Hz, —CH$_3$), 1.1-2.5 (23H, m), 3.33 (2H, t, J=6 Hz, —CH$_2$O—), 3.67 (1H, br s, —CHO—), 4.1 (1H, br, —CHOH—), 5.5 (2H, m, —CH=CH—), 8.3 (2H, br s, OH, CO$_2$H); IR(neat) 3400 br(OH), 1720 (C=O), 1160 (C—O) cm$^{-1}$; $^{13}$C NMR(CDCl$_3$) 177.96, 133.51, 131.23, 131.10, 82.07, 73.08, 68.67, 46.17, 37.07, 33.95, 31.67, 30.89, 29.52, 25.69, 25.03, 24.45, 22.50. 20.68, 17.04, 13.92, 13.79, 12.62; m/z 332.23676 (calcd for C$_{21}$H$_{32}$O, (M.$^+$—H$_2$O), 332.23515).

It therefore can be seen that the invention accomplishes all of its stated objectives.

What is claimed is:

1. A method of synthesis of 7-oxa bicyclic prostaglandin analogs, comprising, reacting norbornadiene palladium dichloride with t-butyl 6-hydroxyhexanoate in an oxypalladation reaction to provide an oxypalladium bicyclic intermediate;

carbonylating said intermediate, in the presence of an organic trialkylamine selected from the group consisting of triethylamine and diisopropylethylamine to provide a bicyclic ester intermediate which in part has the basic prostaglandin analogue carbon skeletal structure; and thereafter selectively hydrolyzing said ester to an acid, reducing said acid to an aldehyde, olefinating said aldehyde by reaction with 2-oxoheptyl phosphonate to provide a keto compound containing the complete carbon skeletal structure of a 7-oxa prostaglandin analog.

2. The process of claim 1 wherein the organic trialkylamine is diisopropylethylamine.

3. The process of claim 1 wherein an additional step comprises reducing said keto group of the olefination product to a hydroxyl group.

4. The process of claim 3 wherein an additional step comprises removing said t-butyl group by ester hydrolysis.

5. A method of synthesis of a 7-oxa tricyclic prostaglandin analogs, comprising, reacting norbornadiene palladium dichloride with t-butyl 6-hydroxyhexanoate in an oxypalladation reaction to provide an oxypalladium bicyclic intermediate;

carbonylating said intermediate to provide a tricyclic ester of the basic prostaglandin analog carbon skeletal structure; and thereafter selectively hydrolyzing said ester to an acid, reducing said acid to an aldehyde, olefinating said aldehyde with 2-oxoheptyl phosphonate to provide an enone, and if desired, reducing said enone group of the olefination product to a hydroxy group.

6. The process of claim 6 wherein an additional step comprises reducing said keto group of the olefination product to a hydroxyl group.

7. The process of claim 6 wherein an additional step comprises removing said t-butyl group by ester hydrolysis.

* * * * *